United States Patent
Hanina et al.

(10) Patent No.: US 11,244,283 B2
(45) Date of Patent: *Feb. 8, 2022

(54) APPARATUS AND METHOD FOR COLLECTION OF PROTOCOL ADHERENCE DATA

(71) Applicant: Ai Cure Technologies LLC, Mount Kisco, NY (US)

(72) Inventors: Adam Hanina, New York, NY (US); Gordon Kessler, Mt. Kisco, NY (US)

(73) Assignee: Ai Cure Technologies LLC, New York, NY (US)

( * ) Notice: Subject to any disclaimer, the term of this patent is extended or adjusted under 35 U.S.C. 154(b) by 247 days.

This patent is subject to a terminal disclaimer.

(21) Appl. No.: 16/546,838

(22) Filed: Aug. 21, 2019

(65) Prior Publication Data

US 2019/0378601 A1 Dec. 12, 2019

Related U.S. Application Data

(63) Continuation of application No. 14/871,843, filed on Sep. 30, 2015, now Pat. No. 10,395,009, which is a
(Continued)

(51) Int. Cl.
*G06Q 10/10* (2012.01)
*G16H 10/60* (2018.01)
(Continued)

(52) U.S. Cl.
CPC ............. *G06Q 10/10* (2013.01); *G16H 10/20* (2018.01); *G16H 10/60* (2018.01); *G16H 20/10* (2018.01); *G16H 40/67* (2018.01)

(58) Field of Classification Search
CPC .............................................. G06Q 50/22–24
See application file for complete search history.

(56) References Cited

U.S. PATENT DOCUMENTS 3,814,845 A  6/1974 Hurlbrink et al.
5,065,447 A  11/1991 Barnsley et al.
(Continued)

OTHER PUBLICATIONS

Ammouri, et al., "Face and Hands Detection and Tracking Applied to the Monitoring of Medication Intake," Computer and Robot Vision, 2008. CRV '08. Canadian Conference, 147(154):28-30, May 2008.
(Continued)

*Primary Examiner* — Robert W Morgan
*Assistant Examiner* — Edward B Winston, III
(74) *Attorney, Agent, or Firm* — Fish & Richardson P.C.

(57) ABSTRACT

A data capture and storage apparatus for use in confirming administration of medication in a clinical trial or other medication administration scenario is provided. The apparatus includes a data capture device for capturing one or more types of data related to administration of a medication, a storage device for storing the captured data and a processor for processing the stored captured data. The processor further includes an analysis element for performing a local analysis of the stored captured data. The processor is further adapted to identify a particular medication prescription regimen in accordance with the clinical trial or medication administration scenario, determine one or more procedures for administering such prescription regimen, identify one or more activity sequences associated with such procedures, capture activity sequences of actual administration of such prescription regimen compare the captured activity sequences to the identified activity sequences to determine differences therebetween, and providing a notice if differences are determined.

17 Claims, 4 Drawing Sheets

Related U.S. Application Data continuation of application No. 12/728,721, filed on Mar. 22, 2010, now Pat. No. 9,183,601.

(51) Int. Cl.

| | | |
|---|---|---|
| *G16H 20/10* | | (2018.01) |
| *G16H 10/20* | | (2018.01) |
| *G16H 40/67* | | (2018.01) |

(56) References Cited

U.S. PATENT DOCUMENTS

| | | |
|---|---|---|
| 5,441,047 A | 8/1995 | David et al. |
| 5,544,649 A | 8/1996 | David et al. |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brundy et al. |
| 5,911,132 A | 6/1999 | Sloane |
| 5,961,446 A | 10/1999 | Beller et al. |
| 6,151,521 A | 11/2000 | Guo et al. |
| 6,154,558 A | 11/2000 | Hsieh |
| 6,233,428 B1 | 5/2001 | Fryer |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2* | 11/2002 | Martin .............. G16H 20/00 705/2 |
| 6,535,637 B1 | 3/2003 | Wootton et al. |
| 6,611,206 B2 | 8/2003 | Eshelman et al. |
| 6,705,991 B2 | 3/2004 | Bardy |
| 6,881,067 B2* | 4/2005 | Tarry .............. A63B 24/0003 434/247 |
| 6,879,970 B2 | 11/2005 | Shiffman et al. |
| 6,988,075 B1* | 1/2006 | Hacker .............. G06Q 10/10 705/3 |
| 7,018,211 B1* | 3/2006 | Birkholzer .......... A63B 24/0003 434/247 |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,359,214 B2 | 4/2008 | Heard |
| 7,395,214 B2 | 7/2008 | Shillingburg |
| 7,415,447 B2 | 11/2008 | Shiffman et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2* | 2/2010 | Crass .............. G16H 50/30 705/2 |
| 7,692,625 B2 | 4/2010 | Morrison et al. |
| 7,747,454 B2* | 6/2010 | Bartfeld .............. G06Q 30/018 705/3 |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2* | 1/2011 | Elsayed .............. A61P 15/18 600/300 |
| 7,881,537 B2 | 2/2011 | Ma et al. |
| 7,908,155 B2 | 3/2011 | Fuerst et al. |
| 7,911,348 B2* | 3/2011 | Rodgers .............. G16H 10/60 340/573.1 |
| 7,912,733 B2 | 3/2011 | Clements et al. |
| 7,956,727 B2* | 6/2011 | Loncar .............. G16H 20/10 340/309.16 |
| 7,983,933 B2* | 7/2011 | Karkanias .......... G06Q 10/02 705/2 |
| 8,144,148 B2* | 3/2012 | El Dokor .............. A63F 13/213 345/424 |
| 8,321,284 B2 | 11/2012 | Clements et al. |
| 8,533,007 B2* | 9/2013 | Egami .............. G16H 10/20 705/3 |
| 8,538,775 B2 | 9/2013 | Skomra |
| 2001/0049673 A1 | 12/2001 | Dulong et al. |
| 2001/0056358 A1 | 12/2001 | Dulong et al. |
| 2002/0026330 A1* | 2/2002 | Klein .............. G16H 20/10 705/3 |
| 2002/0093429 A1 | 7/2002 | Matsushita et al. |
| 2002/0143563 A1* | 10/2002 | Hufford .............. G16H 10/40 705/7.38 |
| 2003/0164172 A1 | 9/2003 | Chumas et al. |
| 2003/0190076 A1 | 10/2003 | Delean |
| 2003/0225325 A1* | 12/2003 | Kagermeier ........ A61N 5/1049 600/407 |
| 2004/0100572 A1 | 5/2004 | Kim |
| 2004/0107116 A1 | 6/2004 | Brown |
| 2004/0155780 A1 | 8/2004 | Rapchak |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2007/0030363 A1 | 2/2007 | Cheatle et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0008112 A1 | 11/2007 | Covannon et al. |
| 2007/0008113 A1 | 11/2007 | Spoonhower et al. |
| 2007/0265880 A1 | 11/2007 | Bartfeld et al. |
| 2007/0273504 A1 | 11/2007 | Tran |
| 2008/0000979 A1 | 1/2008 | Poisner |
| 2008/0093447 A1 | 4/2008 | Johnson et al. |
| 2008/0114226 A1 | 5/2008 | Music et al. |
| 2008/0114490 A1 | 5/2008 | -Pierre |
| 2008/0138604 A1 | 6/2008 | Kenney et al. |
| 2008/0140444 A1 | 6/2008 | Karkanias et al. |
| 2008/0162192 A1 | 7/2008 | Vonk et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0267447 A1* | 10/2008 | Kelusky .............. G06F 3/0487 382/100 |
| 2008/0275738 A1 | 11/2008 | Shillingburg |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 | 2/2009 | Skomra |
| 2009/0095837 A1 | 4/2009 | Lindgren |
| 2009/0127339 A1 | 5/2009 | Needhan et al. |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1 | 2/2010 | Bartfield |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina et al. |

(56) References Cited

U.S. PATENT DOCUMENTS

| | | | |
|---|---|---|---|
| 2011/0141009 | A1 | 6/2011 | Izumi |
| 2011/0153360 | A1 | 6/2011 | Hanina et al. |
| 2011/0161109 | A1 | 6/2011 | Pinsonneault et al. |
| 2011/0195520 | A1 | 8/2011 | Leider et al. |
| 2011/0275051 | A1 | 11/2011 | Hanina et al. |
| 2012/0075464 | A1 | 3/2012 | Derenne et al. |

OTHER PUBLICATIONS

Batz, et al. "A computer Vision System for Monitoring Medication Intake," in Proc. IEEE 2nd Canadian Conf. on Computer and Robot Vision, Victoria, BC, Canada, 2005, pp. 362-369.

Bilodeau et al. Monitoring of Medication Intake Using a Camera System. Journal of Medical Systems 2011. [retrieved on Feb. 18, 2013] Retrieved from ProQuest Technology Collection.

Chen, Pauline W., "Texting as a Health Tool for Teenagers", The New York Times, Nov. 5, 2009, http://www.nytimes.com/2009/11/05/health/0512/899,510 (3 pages).

Danya International, Inc., "Pilot Study Using Cell Phones for Mobile Direct Observation Treatment to Monitor Medication Compliance of TB Patients", Mar. 20, 2009, www.danya.com/MDOT.asp , (2 pages).

Global Tuberculosis Control: A short update to the 2009 report, World Health Organization, (2009) (48 pages).

Huynh et al., "Real time detection, tracking and recognition of medication intake." World Academy of Science, Engineering and Technology 60 (2009), 280-287.

Mintchell, "Exploring the Limits of Machine Vision", Automation World, Oct. 1, 2011 (6 pages).

Osterberg, Lars and Blaschke, Terrence, "Adherence to Medication", New England Journal of Medicine 2005; 353:487-97, Aug. 4, 2005.

Super-Resolution, Wikipedia, (Oct. 5, 2010) (4 pages).

University of Texas, GuideView, Mar. 15, 2007, http://www.sahs.uth.tmc.edu/MSriram/GuideView , (3 pages).

Valin, et al. "Video Surveillance of Medication intake", Int. Conf. of the IEEE Engineering in Medicine and Biology Society, New York City, USA, Aug. 2006.

Wang et al. "Recent Developments in human motion analysis." Pattern Recognition 36 (220) 585-601 (Nov. 2001).

Whitecup, Morris S., "2008 Patient Adherence Update: New Approaches for Success", www.guideline.com, The Trend Report Series, (Oct. 1, 2008) (17 pages).

\* cited by examiner

APPARATUS AND METHOD FOR COLLECTION OF PROTOCOL ADHERENCE DATA

CROSS REFERENCE TO RELATED APPLICATIONS

This application is a continuation, and claims priority of U.S. application Ser. No. 14/871,843, filed Sep. 30, 2015, now U.S. Pat. No. 10,395,009, issued Aug. 27, 2019, titled APPARATUS AND METHOD FOR COLLECTION OF PROTOCOL ADHERENCE DATA; which is a continuation, and claims priority of U.S. application Ser. No. 12/728,721, filed Mar. 22, 2010, now U.S. Pat. No. 9,183,601, issued Nov. 10, 2015, titled METHOD AND APPARATUS FOR COLLECTION OF PROTOCOL ADHERENCE DATA. The content of the prior applications is incorporated herein by reference in their entirety.

FIELD OF THE INVENTION

This invention relates generally to patient compliance in clinical drug trials or other medication administration protocol scenarios, and more particularly to an apparatus for the collection, analysis and transmission of data related to monitoring, instruction and intervention of patients in clinical trials or other medication administration protocol scenarios in order to improve adherence with prescribed drug protocols in accordance therewith.

BACKGROUND OF THE INVENTION

Dr Lars Osterberg, M.D. and Dr. Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series*, 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication.

Traditionally, participants attend introductions and follow ups for clinical trials in-person. Other patients attempting to adhere to a particular medication protocol similarly are given a prescription and a particular set of instructions from a prescribing medical provided or prescribing doctor, and then compliance is measured at a next visit with that prescribing professional. Thus, data collection is similarly limited to patient visits, rather than on a daily basis. Old methods such as patient questioning and pill counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times.

Jo Carol et al. stated that "The most reliable method for research purposes, although not practical in a clinical setting, may be a combination approach that includes pill counts, patient self-report, and electronic monitoring." (Carol J. et al. Patterns to Antiretroviral Medication, The Value of Electronic Monitoring, AIDS, 17 (12), pp1, 763-767, October 2003. To date, technologies alone have only been used to monitor compliance rather than to encourage it. Furthermore, there has been no comprehensive system provided that allows for the management of multiple patients and multiple patient populations. While current technology may allow poor compilers to be recognized, as will be described below, the proposed apparatus and method of the present invention will help to encourage pharmaceutical compliance and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact ingesting or otherwise properly administering required medication as required in a clinical drug trial, or as prescribed by a prescribing physician in the case where adherence to a particular regimen may prove to be critical to efficacy of the prescription regimen. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Finally, this system is expensive and requires constant maintenance to confirm that the various mechanical parts are in working order.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or the relationship of adherence to the efficacy of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration.

Therefore, it would be desirable to provide an apparatus that overcomes the drawbacks of the prior art.

SUMMARY OF THE INVENTION

In U.S. patent application Ser. No. 12/620,686, filed Nov. 18, 2009, titled Method and Apparatus for Verification of Medication Administration Adherence; currently pending, U.S. patent application Ser. No. 12/646,383, filed Dec. 23, 2009, titled Method and Apparatus for Verification of Clinical Trial Adherence, currently pending; and U.S. patent application Ser. No. 12/646,603, filed Dec. 23, 2009, titled Method and Apparatus for Management of Clinical Trials, currently pending, the contents of these three applications being incorporated herein by reference, the inventors of the present invention have proposed a system and method that allow for complete control and verification of adherence to a prescribed medication protocol or machine or apparatus use in a clinical trial setting, whether in a health care provider's care, or when self administered in a homecare situation by a patient.

These applications present the only medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings.

In accordance with the present invention, an apparatus is provided that facilitates information presentation to a patient, information capture of medication administration at home in a homecare setting, in a hospital setting, in a clinical trial setting, or in any other setting in which medication adherence is potentially an issue, and other aspects described as part of the method and system of the pending applications noted above. Therefore, in accordance with the present invention, a video capture device is provided including a memory for storing captured video and other patient data, analyzing such captured data, transmitting such captured data to a remote location, receiving information from a remote location and providing information to the patient as preferred in accordance with the present invention. In accordance with a preferred embodiment of the invention, an apparatus is provided comprising a video capture device, an audio capture device, memory for storing such captured data, a processor adapted to operate analysis software for analyzing the captured data, a transmitter for transmitting the captured data, or other versions of the data or analysis results to a remote location, for receiving data and further instructions or communication from the remote location, and a display for providing such data or further instructions to the patient. Such apparatus may preferably interface with management software adapted to manage multiple patients, and thereby providing a full monitoring and data collection procedure.

The novel combination of text, graphical pictorial, and video presented in accordance with the present, and as further described in the above noted applications allows the compliance problem within clinical trials and other patient monitoring of adherence to medication protocols to be tackled in a holistic manner. The present invention provides an apparatus that presents a number of solutions. The apparatus preferably may provide step-by-step image and video instructions to the user or care provider on how to administer medication, what the side effects of the medication are and the benefits that have been found. This avoids misunderstandings resulting from prescribing instructions and may allow an approach that may be utilized internationally, thus overcoming possible language barrier issues and the like.

A specific medication regimen may be programmed into a medication calendar included within the apparatus constructed in accordance with the invention to alert the user when medication should be taken and provide clear video instruction for taking the medication. These reminders minimize forgetfulness by the subject in clinical trials or when administering medication in a typical home setting, and help the logistical challenges involved in complex medication regimen such as double blind studies, for example. Furthermore, the medication calendar and the compliance results are accessible to the clinical trial organizers.

Once an alert is provided by the apparatus of the invention and the patient has confirmed that they are ready to take the medication, the apparatus is adapted to record the type of medication and quantity through image recognition. The subject may show the medication to the imaging device of the inventive apparatus which then authenticates the medication if in the correct dosage and offer administration instructions. Other types of recognition of the bottles may also be used, including RFID tags, bar code reading, text recognition, or other confirmation through a provided graphical user interface, preferably in conjunction with the image recognition. Once the medication type and quantity has been authenticated, the apparatus if the invention records or otherwise visually analyzes the patient actually administering the medication to him or herself, using any of the above recognition methods, and further including facial recognition, badge identification, or any other method for confirming the identity of the individual. A real-time log for audit trails and further analysis is thereby created. Additional information may be captured using a brief questionnaire on the device which may help to highlight problems when administering the medication—such as difficulty in swallowing tablets or opening packages—or adverse reactions from which the patient is suffering. Whatever the reason a patient misses a reminder or medication prompt, the system and method of the invention alerts the clinical trial organizers. Data from all the population can be captured and presented in an aggregated manner online in real-time, giving real-time data results and flag problems or results early.

It is therefore contemplated that the apparatus in accordance with the present invention be applicable to settings including clinical trials, as well as in more general healthcare settings, such as with home care provided by a healthcare assistant, or self administered by a patient, in a hospital or other clinic setting, or in other locations where medication management would be beneficial. The ability for the apparatus constructed in accordance with the invention to capture patient and medication administration data in a more controlled environment will allow for more consistent data to be gathered, thus easing the burden of insuring adherence to one or more prescribed medication administration regimens.

Furthermore, while the apparatus constructed in accordance with the application has been described as implementing a method and system as described in one or more other pending US patent applications, it is intended that the apparatus be available as a standalone apparatus, for use and implementation in systems other than those described in accordance with this or other noted patent applications.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of pans that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
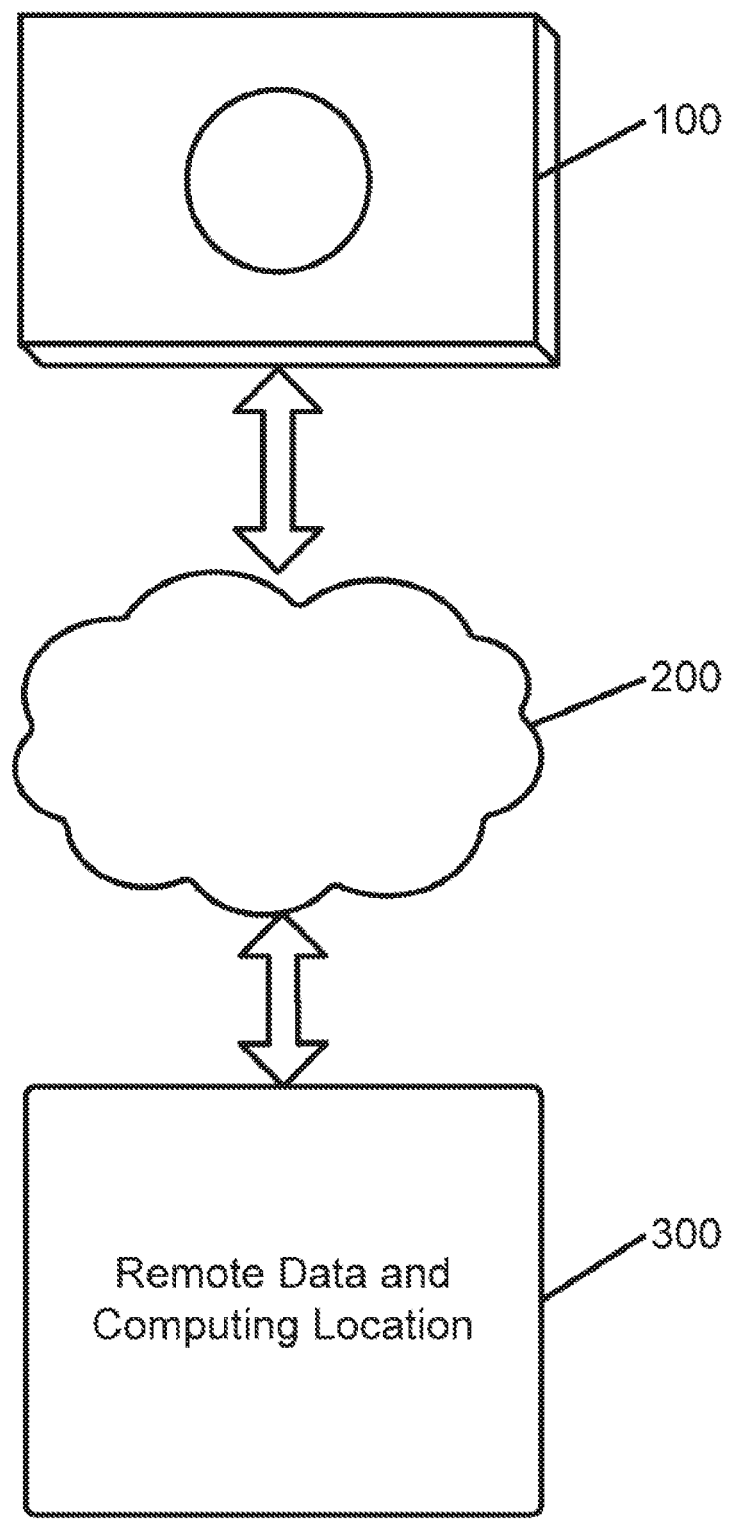
FIG. 1 is a block diagram depicting an embodiment of the invention.

Referring first to FIG. 1, a remote information capture apparatus 100 is shown. Such apparatus is adapted to allow for the capture and processing of information in order to implement the system and method in accordance with the applications noted above and incorporated herein by reference. Such information capture apparatus 100 is placed in communication with a remote data and computing location 300 via a communication system 200, preferably the Internet or other communication system. Via communication system 200, information captured by apparatus 100 is transmitted to remote data and computing location 300, and analysis information or other instructions may be provided from remote data and computing location 300 to apparatus 100. It is further contemplated that a plurality such information capture apparatuses 100 may be coordinated to monitor a larger space than a space that can be covered by a single such apparatus. Thus, the apparatuses can be made aware of the presence of the other apparatuses, and may operate by transmitting all information to one of the apparatuses 100, or these apparatuses may each independently communicate with remote data and computing location, which is adapted to piece together the various information received from the plurality of devices 100.

Figure 2:
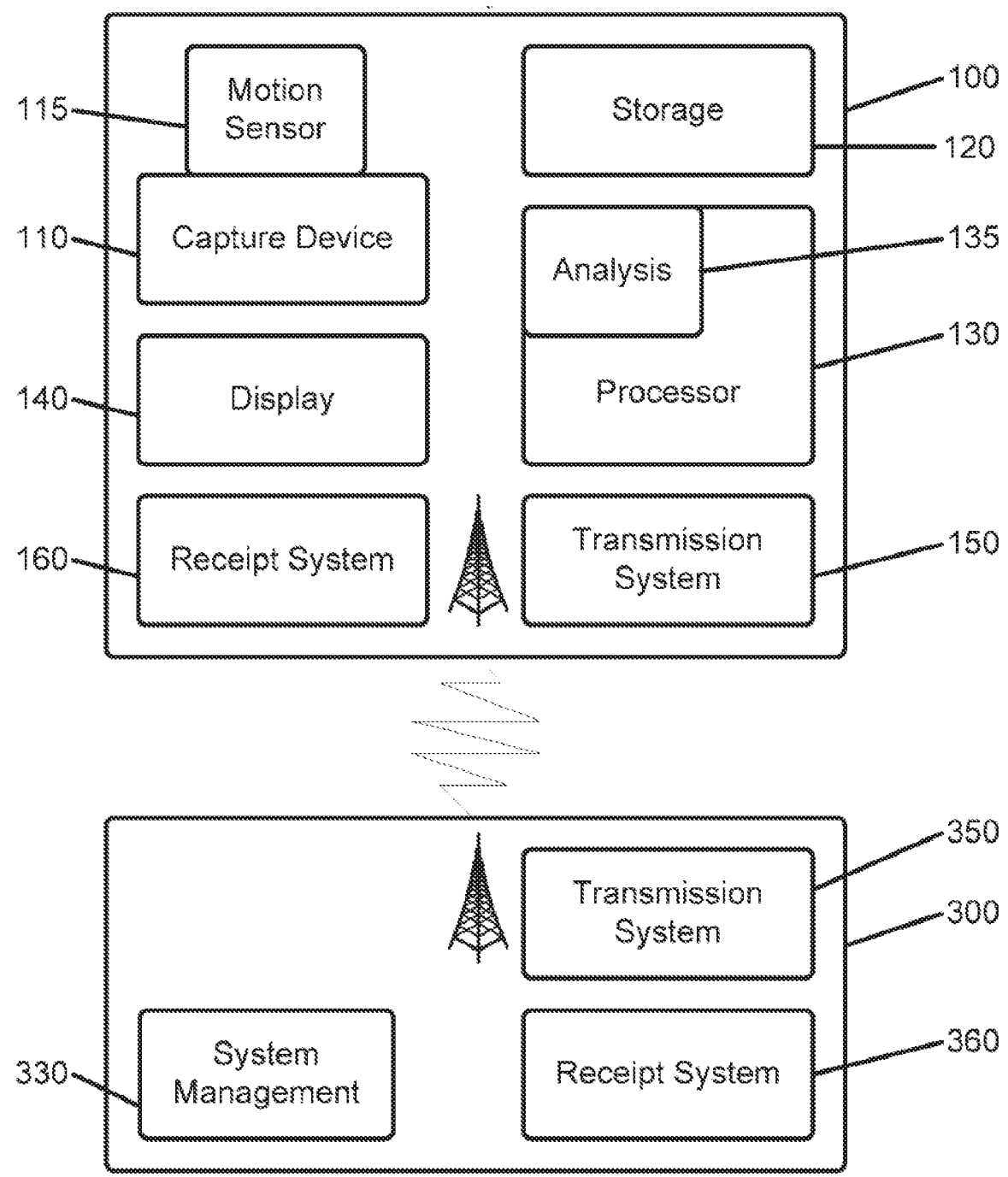
FIG. 2 is a block diagram depicting details of systems associated with an embodiment of the invention.

Referring next to FIG. 2, a more detailed view of a preferred embodiment of remote information capture apparatus 100 and remote data and computing location 300. As is shown in FIG. 2, apparatus 100 comprises an information capture device 110 for capturing video and audio data as desired. A motion detector 115 or other appropriate trigger device may be provided associated with capture device 110 to allow for the initiation and completion of data capture. Information capture device 110 may comprise a visual data capture device, or may be provided with an infrared, night vision, or other appropriate information capture device. A storage location 120 is further provided for storing captured information, and a processor 130 is provided to control such capture and storage, as well as other functions associated with the operation of remote information capture apparatus 100. An analysis module 135 is provided in accordance with processor 130 to perform a portion of analysis of any captured information at the remote information capture apparatus 100. Apparatus 100 is further provided with a display 140, and a data transmission and receipt system 150 and 160 for displaying information, and for communicating with remote data and computing location 300. Remote data and computing location 300 comprises system management functions 330, and a transmission and reception system 350 and 360 for communicating with apparatus 100. Such system management functions comprise, at least in part, many of the centralized functions noted in the three pending patent applications noted above and previously incorporated herein by reference. Transmission and reception system 350 and 360 may further comprise various GPS modules so that a location of the device can be determined at any time, and may further allow for a message to be sent to one or more individual apparatuses, broadcast to all apparatuses in a particular trial, or being used for administration of a particular prescription regimen, of broadcast to all available apparatuses.

In accordance with the invention, apparatus 100 is adapted to be part of a system that improves adherence to medical protocol in both a clinical trial and other medication administration setting. Users of apparatus 100 in accordance with this system give administrators a tangible and concrete manner in which to confirm compliance or lack thereof, and the ability to intervene early in the process to ensure that patients enrolled in such a clinical trial study are properly taking their medication. Apparatus 100 of the invention is adapted to receive instructions for patients from remote data and computing location 300 and provide these instructions to patients on the use of the prescription medication. Such instructions may comprise written, audio or audio visual instructions for guiding a user to adhere with a prescribed protocol. Apparatus 100 further provides verification to a doctor or other service provider of patient adherence to the prescribed protocol, and statistical and individual analysis of adherence rates to ensure proper medication administration.

Figure 3:
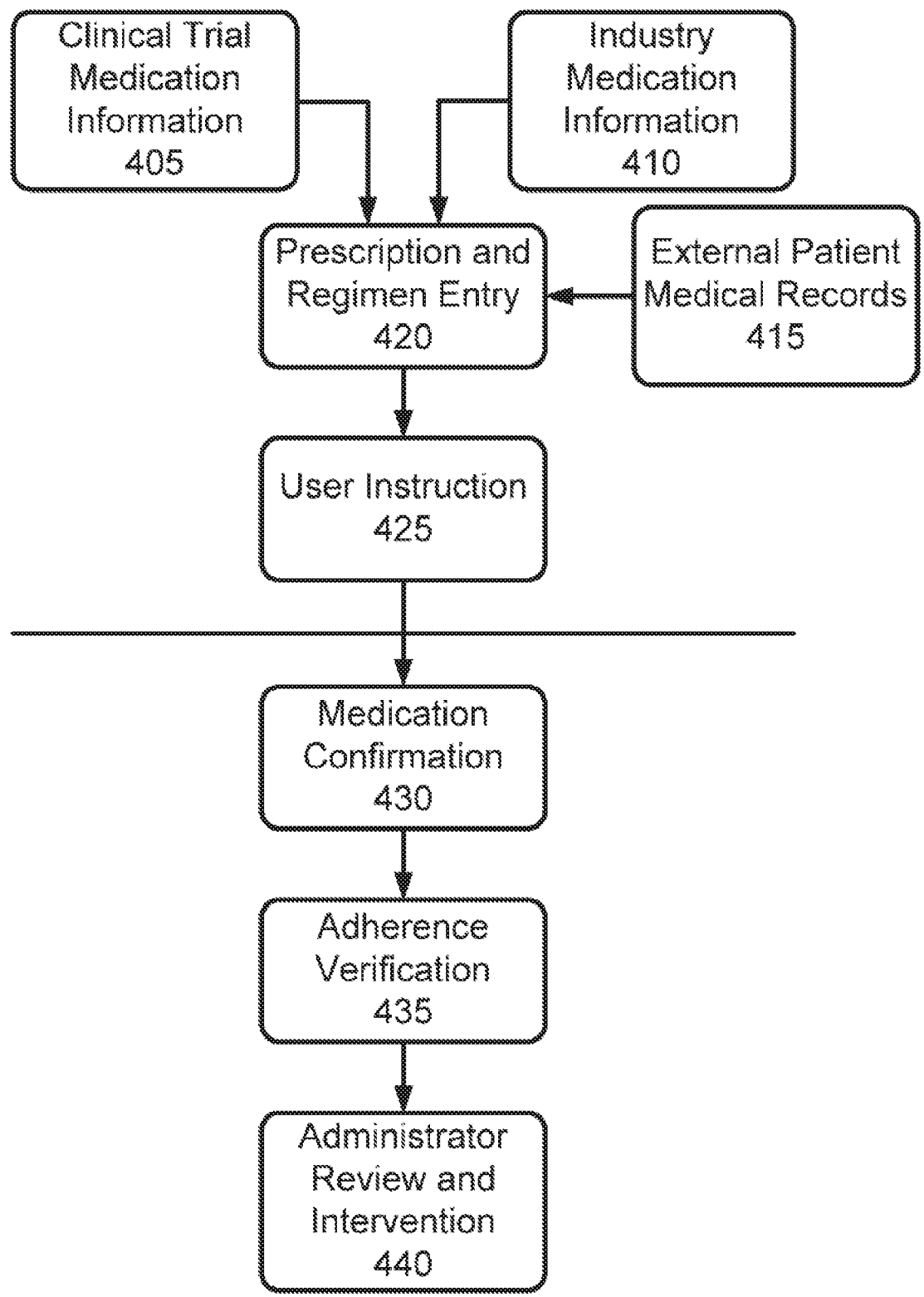
FIG. 3 is a flow chart diagram depicting a method in accordance with an embodiment of the invention.

Referring next to FIG. 3, a data flow overview on accordance with the operation of apparatus 100 is shown. In accordance with the invention, information about a particular drug to be the subject of a clinical trial or other medication administration program or prescription is provided in a database 405, and existing industry medication information databases 410 are employed to access prescription, interaction, application and other available information about any number of proposed prescription and non-prescription medications and their possible interaction with the clinical trial medication. Further, patient medical records 415 are used, and as will be described below, are used in conjunction with the industry medical information and a medical professional's prescribing expertise to confirm that a patient is a good candidate for such a clinical trial. These databases may be accessed via apparatus 100, or from remote data and computing location 300. Once confirmed, a medicine regimen in accordance with the clinical trial or other prescription requirements is prescribed and entered into the system of the invention at 420. Once entered into the system, a particular prescription regimen causes a set of user instructions 425 to be generated and transmitted to apparatus 100. In a clinical trial setting, such instructions may be varied for different users to determine the best set of instructions, or may be varied based upon demographics, experience, or other factors that may require different types of instructions to be provided. It is further contemplated in accordance with the invention that multiple clinical trials or patient populations may be managed by a manager in accordance with the invention so that the invention contemplates a medication administration system that allows for a single point of management for all clinical trials or patient management groups associated with a particular manager or the like.

Such user instructions may include general instructions about the particular medication subject to the current trial or medication administration protocol, methods for ingestion, warnings about side effects, concerns about drug interactions with common substances or medications, or other medications prescribed to the patient by the system or by another medical service provider. It is contemplated in accordance with the invention that such set of user instructions may be interactive, allowing a user to view additional information about such instructions or prescriptions as desired. These instructions may comprise written, audio or video instructions provided to the user on display 140 of apparatus 100. Furthermore, it is contemplated in accordance with the invention that at various points during the instruction set, for example when a patient asks a particular type of question, or asks to receive additional information about a particular aspect of the medication or prescription regimen through entry of information into apparatus 100, that apparatus 100 may reach out and contact a representative of a medical service provider via the transmission and reception systems 150 and 160 to provide the patient with additional, personal help as necessary, if it is determined that such intervention by the medical professional would be desirable to the patient. Thus, such a patient may be assisted in properly taking medication so that various errors do not take place. Indeed, in more traditional scenarios, it is only after perhaps finishing a prescription regimen and a return to a doctor in accordance with a predetermined clinical trial schedule that it is discovered that the medication may have been taken incorrectly. In accordance with the present invention, early intervention with such issues can be exercised to deter any possible unfortunate outcomes from improper administration of medication, and to ensure that the particular patient is able to remain in the study and provide accurate data to the study.

It is contemplated in accordance with the invention that a touch or other user friendly graphical user interface be provided associated with apparatus 100 so that the user can easily manipulate any number of prescription factors, and perhaps enter additional information that may be useful to a prescribing medical provider, such as level of fatigue, level of hunger, jitter inducing medications, etc. All of these data collection points allow for a smoother administration of medication to a patient, and therefore a more likely chance of adherence to a prescribed protocol.

Referring to the lower portion of FIG. 3, the horizontal line indicates a time for patient ingestion or other administration of medication. The patient may display a medication container and/or an actual pill or other medication form to imaging capture device 110 of apparatus 100 at step 430, which in turn may perform local processing and analysis via processor 130 and associated analysis module 135. Apparatus 100 confirms that the medication is correct and is the currently prescribed medication to be taken through the use of text recognition, pill recognition, or other appropriate medication recognition scheme. This sequence of steps therefore acts as an audit trail each time a medication is taken, that can be reviewed later, to ensure that a patient is properly following a regimen.

In accordance with the invention, confirmation of patient adherence to the prescribed administration schedule for the medication as prescribed by the clinical trial or other prescription regimen is determined. While such confirmation may take a number of forms, in accordance with the invention, a preferred method for such confirmation may include capturing a video sequence of the patient actually administering the medication by apparatus 100. In a further preferred method, such a sequence for such confirmation may include employing a facial recognition sequence or other biometric confirmation that a particular patient is in fact receiving treatment, but may also provide for the ability to obscure the race or other identifying feature of a user to allow for the storage and use of such images while protecting the identity of the patient, a technique that may be beneficial when a manager is providing a general report about the clinical trial, and not trying to remedy a situation with a particular patient. Activity recognition, gesture recognition or other feature for determining whether a particular subject movement meets a predefined movement sequence may be employed to be sure that the patient is properly taking prescribed medication.

Furthermore, in accordance with the present invention, a video image of the patient actually administering or ingesting the medication may be taken in accordance with apparatus 100 and stored in memory 120 so that actual confirmation may be achieved, rather than simply relying on the patient to state that a particular medication was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are property administering the medication according to the protocol, thus reducing the possibility of the potential appropriate movements considered to be "correct." Indeed, various instructional videos or other appropriate training may be provided to a user to insure they properly administer the medication. Finally, in accordance with the invention, if recording of a video of a patient having the medication administered thereto is not possible, the system of the invention will recognize such an issue and request audio confirmation via apparatus 100 as a next best option, if the audio confirmation is also not possible, then a less reliable method of confirmation, such as a keyboard confirmation by the patient may be accepted. If higher reliability methods of confirmation are not available for an extended period of time, an alarm is preferably forwarded to a medical professional to inquire as to reasons and to remedy any situation that might be wrong in the administration situation.

These steps of confirming identity, confirming medication and confirming administration are then reviewed to verify adherence to the prescribed protocol at 435. Such review is preferably performed automatically first by processor 130 and analysis component 135 thereof that is able to align the actual recorded images with ideal or expected images, or through the use of other activity or gesture recognition as mentioned above. In the case of facial recognition and bottle or pill recognition, such techniques are known in the art. With regard to video confirmation of adherence to prescribed medicine administration procedures, such processing may include various stick figure comparison analyses, activity recognition analysis, or other schemes as noted above able to determine whether appropriate actions have been performed by the patient.

The ability to provide automated determination of adherence to proper administration procedures at the apparatus 100 allows tor a first, quick review of any such images to determine whether any immediate attention may be warranted. As will be described below, further review at remote data and computing location 300 allows for a large number of such images to be reviewed in a short period of time. Even if actual and complete lack of adherence is not able to be determined 100% in each possible situation, the ability to pre screen the administration video captures to remove from further consideration administration situations that are clearly compliant may reduce a number of compliance situations to be reviewed by a medical professional substantially. Additional human review of indications of failure of adherence may be provided, thus insuring proper review of all potentially dangerous situations while greatly reducing the number of images necessary to be reviewed by a human. Thus, multiple benefits of such an automated system are realized, including reducing time to review such images, reducing costs of such review, and improving patient privacy by limiting the number of humans viewing such data, while improving quality.

In an additional embodiment of the invention the imaged sequences used for activity recognition to determine regimen adherence may be further used to check for adverse or other reactions to taking of the medication. Thus, in addition to simply determining proper adherence to a protocol at apparatus 100, such activity or gesture recognition may determine any number of different actions that may have been taken by a patient. Thus, actions taken before medication administration, or actions taken after medication administration may give insight into reasons for particular responses, etc. Thus, before administration, in accordance with the invention, activity recognition may determine a current activity of a user. Any subsequent reminders to take a medication may in part be based upon this determined activity. By way of example, if a user is putting on a coat, or is determined to be leaving a residence or other facility or the like, a reminder to take a medication before leaving may be provided, even if earlier than normal, or if medication is portable, the user may be reminded to take the medication with them, and then subsequently reminded to administer the medication via notification on a mobile device. By way of further example, if the user is cooking, a reminder may be given to take the medication a predetermined time before eating. Other scenarios may be possible, thus allowing greater response from the system to ensure proper medication administration by a patient. Additionally, various patient consent issues may be prompted and recorded in accordance with the invention. Patients may ask further additional questions regarding such consent, thus insuring that patients have all of the information they need to make informed consent decisions, and medication providers have proper evidence of such consent.

Similarly, actions after taking medication may give insight into patient responses. Notice of fainting, falling down, lack of motion, facial gestures, gastrointestinal distress or the like may all be logged as adverse reactions to a particular medication regimen, and may allow for adjustment of dosage or prescription instructions in the future for the patient. If adverse reactions are severe, an immediate medication review and contact from a medical professional may be provided to cure the issue. Additionally, the system in accordance with the present invention may be directly tied and be interoperable with a pharmacy or medical provider's systems as administered by the clinical trial manager, thus allowing such recommendations for dosage changes, regimen changes and the like to be forwarded to these professionals automatically. Through such links, reordering medication, dosage changes, medication changes and the like may be automatically provided. Furthermore, ease of providing additional prescriptions can be enhanced as patient, medication and regimen information will already be available to the pharmacist or medical service provider.

After such automatic, or combination of automatic and manual, adherence verification is performed allowing a health care provider or other medical professional to review and verify results of the automatic comparison or direct review of captured activity sequences, and indication of variation from a desired identity, medication or application procedure may request administrator review of the situation, and intervention as may be determined necessary at 440.

Such review may be required immediately as an emergency situation may exist, or the patient may gesture or otherwise indicate that help is necessary, or such review may be less urgent, perhaps requiring an electronic communication with suggestions or the like from such an administrator or the like. Additionally, such adherence review may be stored over time for a particular patient, thus allowing for various medication trends to be determined, such as if a patient misses medication at a same time each week, or an indication that one particular health care worker aiding the patient may occasionally give an incorrect medication dosage amount. Thus, in addition to allowing for immediate notice of problems in medication administration, an audit trail for tracking the actions of various health care providers is generated. Such an audit trail allows clinical trial administrators or other medical professional to determine immediately, or upon review of a complete medication regimen, whether a particular patient or group of patients has followed the protocol to the level that allows their results to be used as part of the study. Additionally, levels of adherence may give insight as to the ease of use of a particular regimen, and whether instructions provided to the patient are sufficient to allow for adherence to the prescribed medication regimen.

Figure 4:
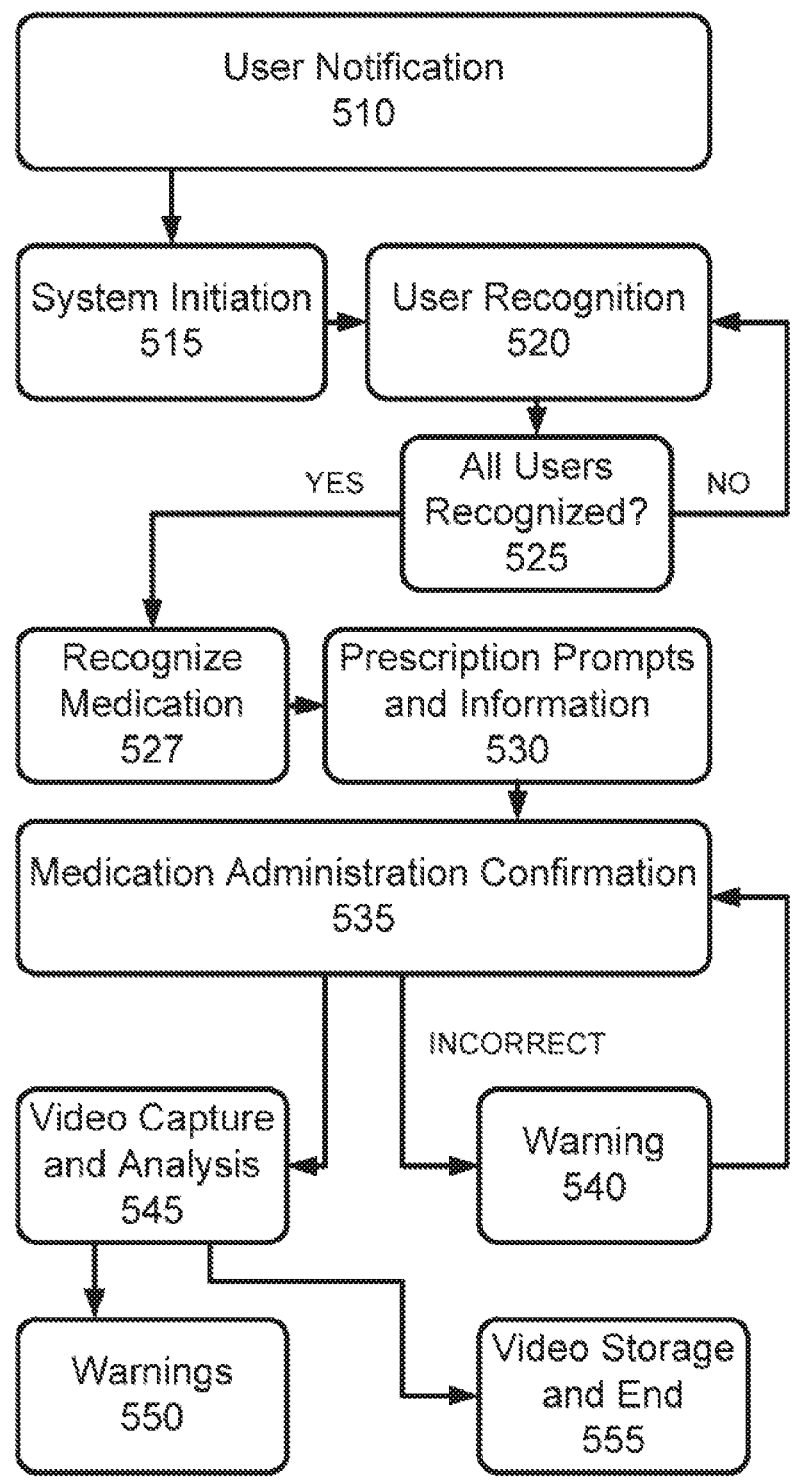
FIG. 4 is a flow chart diagram depicting a method in accordance with an embodiment of the invention.

Referring next to FIG. 4, a user implementation of the method in accordance with the invention will be described. When a time for receiving or administering a medication in accordance with a clinical trial regimen is reached, a patient, and any other necessary user may be provided a notification 510 from apparatus 100. Thus, in a home situation, only the patient may receive notification. If there is a home health care provider, such provider may also receive separate independent verification. In the case of hospital or other in-patient care facility, various medical service providers may similarly receive such notification. After notification, or in the absence of such notification, system initiation preferably takes place at 515. In accordance with such system initiation, one or more users are preferably recognized by the system. Therefore, at step 520, a user recognition sequence may be employed. In a preferred embodiment, such a user has a still or video image captured of their face by apparatus 100, and facial recognition techniques are employed to confirm the identity of the user in analysis module 135. Alternative recognition techniques, such as retinal, fingerprint, voice or other biometric measurements may be employed, in addition to a more common password query. Any other appropriate identification technique may be employed, and any unique individual identifiers may be obscured, as noted above, when the images are to be used as a more general report regarding adherence, rather than an individual patient response.

At step 525 it is determined whether all necessary users have been recognized and authenticated. In a situation where a nurse, doctor or other caregiver is to administer medication, it may be preferable to have the patient and caregiver to be recognized by the system to further confirm that the appropriate procedure is followed, and to allow the system to keep track of people using the medication so it can track if any one person, for example, is improperly using the medication, as will be evident from the generated audit trail. After step 525, if all users are not recognized, control passes back to step 520 and any additional users are recognized by the system.

Once all users are recognized, control passes to step 527 where the medication to be administered in accordance with the prescribed prescription regimen of the clinical trial is confirmed. Thus, a user is prompted by apparatus 100 to allow a still or video image, text recognition image, or other method of identifying a medication to be captured of the medication bottle or other container, a pill of the medication, or other form of medication, and is also able to determine appropriate quantities, dosage, and any potentially required or dangerous medication combinations. As noted above, if video confirmation is for some reason not available, the user may be prompted by the system to provide audio or other indication of medication and other desired information. This image, video sequence or other received confirmation information is then compared to an image associated with a prescribed prescription. If the medication is determined to be incorrect after analysis by analysis module 135, a warning may be provided from apparatus 100 to the user that the medication is incorrect. The user may then be prompted to choose another medication for imaging.

Alternatively, the invention contemplates a user displaying a number of medications to apparatus 100 and allowing the apparatus to suggest which medication is correct. Thus, the user may be able to scan a medicine cabinet with such a video imaging apparatus and have the system indicate which the correct medication is. This may prove valuable when sequence of ingesting medication is important, or when two people have similar medications and may have difficulty in distinguishing between medications for each. Once a correct medication has been identified, control passed to step 530.

In step 530 user prompts and other instructions are provided to the patient from apparatus 100, and present caregivers, as to how to administer die medication according to the prescription guidelines outlined above as determined in accordance with the particular clinical trial under consideration. These instructions allow for a user to receive further information or instructions as necessary through asking the system for additional help. Especially in situations where an elaborate scheme may be required, it is contemplated that video samples and instructions may be provided to the user. Further, in accordance with the invention, for complicated administration procedures, it may be possible to set up a two way video conference employing traditional video conferencing, VOIP conferencing, traditional telephone conferencing, or any other appropriate communication system with an expert in such administration so that a caregiver or patient may receive live coaching regarding such administration, all via apparatus 100, perhaps with additional features and elements provided to allow for such additional functionality. Such instructions and prompts may be determined by the medication manager to determine the success or failure of particular sets of instructions. Thus, not only may medications tested in a clinical trial, but also sets of instructions are tested to determine which are best for all, or for giver demographic groups or the like for eventual user when the medication is released to the public, thereby allowing for a better adherence rate by the public. As the number of clinical trials and other patient populations grows, and the locations of such trials groups become more international, such administration through a system such as that set forth in accordance with the invention may become far more important to various medication administration managers.

When following such instruction prompts, the actual act of administration is preferably captured as a video sequence at step 535 by apparatus 100 via capture device 110 and stored to storage 120. Administration preferably includes one or more identifiable gestures as suggested in accordance with the instructions above. A patient or administrator may be provided with one or more images or sequences for method of application or administration, and thus the following of these sequences is used to determine compliance with a particular prescribed regimen. Further, long gaps or pauses may be determined to give further insight into areas of administration that may be giving problems to administrators of trial participants. This captured video sequence may be utilized in accordance with the invention in a number of ways. First, the actions of administration of the medication is reviewed in real time and compared to an ideal or desired video sequence by processor 130 and analysis module 135. If a determination is made that the medication is being administered in an incorrect manner, and in a way that may be detrimental to the patient, immediate warnings may be provided at step 540 via apparatus 100 advising the caregiver or patient to stop administration at once. Furthermore, in extreme cases, a doctor or other caregiver may be notified, or in the most dangerous cases, an ambulance or other emergency personnel may be dispatched to provide immediate care.

Notification may also be provided to the clinical trial manager or other medication administrator so that this person is warned that one or more patients are having problems with adherence with the protocol. If such problems turn out to be isolated, alternative instructions, or personal help may remedy the situation, thus allowing the person to provide meaningful data to the trial. If such lack of adherence is for more widespread, a clinical trial manager or other medication administrator may change instructions for all participants, or may even ask all participants to come back in for further live instructions. In either situation, the cost of administration is greatly reduced as participants are able to remain in a study, and major failures of studies for lack of protocol adherence may be avoided. Reports based upon such widespread lack of adherence may provide a manager with a report, using images or the like with identifying features removed so that the report may show precisely how a medication is being administered while maintaining patient privacy and confidentiality. If video recording is not available, other confirmation methods as noted above may be employed and be subject to automatic confirmation as with the video recorded sequences.

If such immediate care or warning is not required, control then passes to step 545 where the video images are more formally captured, transmitted to remote data and computing location 300 and analyzed for various other non-critical issues. The images may be captured and stored locally, being provided to a central server in a batch processing, or images may be captured and sent to the remote server location 300 for immediate analysis and storage. Such analysis may consider suggestions to a caregiver to improve dosage accuracy, reduce pain in administration, or the like. Furthermore, as such video sequences may be available from multiple patients and/or caregivers taking part in a current or multiple clinical trials, the effectiveness of various sets of instructions and the like can be tested and reviewed, and changes thereto made if consistent problems are encountered. This type of study is nearly impossible without the present invention, because in any type of clinical setting, individuals are far more likely to be careful in administration of medication, and therefore not cause errors. When they return home or back to their regular lives, this is when adherence and administration issues arise. In accordance with the invention, responses to instructions can be analyzed, and lack of adherence based upon confusing or difficult to follow instructions can be remedied, providing better or more usable instructions, and therefore improving regimen adherence. Without the present invention, such a clinical trial manager may be unaware of such issues. With the invention, these issues can be addressed as they arise, thus ensuring the integrity of the clinical trial.

In any event, after such analysis, any warnings or suggestions for instruction issues may generate a warning at step 550, suggesting areas of instruction that may be problematic. These video sequences are also stored for longer term analysis if desired at step 555, and processing ends. Furthermore, in order to encourage patients in the clinical trial, notices of lack of adherence may be used to change remuneration received by a patient in the clinical trial. Thus, adherence to the protocol results in higher payments to the patient, a great incentive for the patient to adhere to the protocol.

Trends of a patient taking part in the clinical trial or other medication administration program can be monitored by apparatus 100 in accordance with the provision of additional diagnostic attachments, such as blood pressure or other measurable quantities of the patient, and correlation between such measured quantities and medication administration may be observed, potentially allowing for a more customized solution of medication to be applied to the patient, possible modifying dosage or frequency of administration based upon individual reactions to a particular prescription regimen. Additionally, features of the invention noted above allowing for user interaction and recordation of activities of a user, adverse effects and the like may be incorporated into the system to provide further information for determining alternative instruction sets, modification of medications and the like.

Thus, provision of such an apparatus 100 increases effectiveness and allows for better control over medication administration. Difficulties in following protocols may be determined in near real time. Changes in a medication protocol may be easily implemented and conveyed to patients and their prescribing doctors. New training modules, including video, written, or other instructions may be provided improve adherence. Inventory management is eased and all patients are sure to have the appropriate amounts of medication and other supplies. The system and apparatus 100 can be used by a single medical provider, doctor group or network, insurance company, governmental agency, nursing home, hospice, home care provider or the like, or other group in order to track any number of patients and associated home care workers, doctors, or other medication administrators.

All communications in accordance with the invention are preferably encrypted or otherwise protected during transmission and storage at both local and remote mass storage location to meet any security issues and any regulations required for the storage and maintenance of medical and patient health care information.

Alternative embodiments of the invention may provide one or more of the following additional features. Rather than simply providing a video capture in a traditional sense, apparatus 100 may be provided with night vision, infrared vision, or other desired capture scheme. Apparatus 100 is also contemplated to be provided with a number of apparatus management features, including an ability to choose between color and black and white video storage and transmission, auto focus on a patient or the like, and including tracking of such an individual as they move about a room, the ability to strip any identifying information from transmitted video so that anonymity can be maintained, if desired. Apparatus 100 may include mechanisms to indicate a need for recharging, and include sleep modes for extending battery life. It is further contemplated that apparatus 100 may act as a monitoring device for a patient, and in a standby mode the apparatus may "listen" or "look" for sounds from the patient, including suggestions of a fall, scream or the like. Automated responses may be provided in order to access patient status via integrated speakers or the like. The transmission system of apparatus 100 may then notify appropriate personnel. Thus, the portability and multiple use areas provide an additional benefit to the user of this apparatus.

Therefore, in accordance with the invention, a method and apparatus are provided that allow for the automated confirmation of adherence to administration protocol for medication, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed is:

1. A medication adherence monitoring system, comprising:
    a first storage device operable to store one or more sets of user prompts for encouraging proper performance of one or more predetermined movement sequences indicative of proper medication administration;
    a display operable to display, to a patient, one or more of the one or more sets of user prompts for encouraging proper performance of the one or more predetermined movement sequences;
    a video data capture device operable to capture, as captured video data, at least video data of the patient performing one or more of the one or more predetermined movement sequences in response to the one or more of the one or more sets of user prompts;
    a second storage device for storing the captured video data; and
    a first processor operable to
        output, to the display, a first type of alert that notifies the patient it is time to administer medication,
        receive a patient medication administration initiation response following the output of the first type of alert,
        output to the display, responsive to receiving the patient medication administration initiation response, the one or more of the one or more sets of user prompts for encouraging proper performance of the one or more predetermined movement sequences,
        receive the captured video data from the second storage device,
        automatically compare, as a comparison, the captured video data to additional video data comprising video of the one or more of the one or more predetermined movement sequences,
        determine, from the comparison, whether the patient has properly performed the one or more of the one or more predetermined movement sequences,
        responsive to determining, from the comparison, that the patient has not properly performed the one or more of the one or more predetermined movement sequences, output, to the display, interactive feedback to the patient and an additional one or more of the one or more sets of user prompts to further encourage proper performance of the one or more of the one or more predetermined movement sequences.

2. The system of claim 1, further comprising a transmission system for transmitting the captured video data to a storage and analysis location that includes the first and second storage devices, and the first processor and that is remote from the video data capture device.

3. The system of claim 1, wherein the first processor is operable to, in response to the comparison of the captured video data to the additional video data, determine whether an immediate first response to the patient would be proper, and
    subsequent to determining that the immediate first response to the patient would be proper, output to the display a second type of alert.

4. The system of claim 3, further comprising:
    a storage and analysis location that includes a second processor and that is remote from the video data capture device; and
    a transmission system for transmitting the captured video data to the storage and analysis location, wherein the second processor is operable to recognize and analyze medication administration including medication ingestion by the patient from the captured video data, and wherein the second processor is operable to, in response to analyzing the captured video data, determine whether a second supplemental response to the patient would be proper.

5. The system of claim 4, wherein the second processor is operable to transmit, by the transmission system, the second supplemental response from the storage and analysis location to the display.

6. The system of claim 1, further comprising:
    a transmission system operable to transmit the captured video data to a storage and analysis location that is remote from the video data capture device; and
    a receipt system operable to receive medication adherence response information from the storage and analysis location.

7. The system of claim 1, wherein the one or more predetermined movement sequences comprises an activity associated with administration of a prescription protocol.

8. A medication adherence monitoring system for use in confirming administration of medication in a clinical trial, comprising:
    a first storage device operable to store one or more sets of user prompts for encouraging proper performance of one or more predetermined movement sequences to be performed by a participant indicative of proper performance of a predefined participant clinical trial protocol for medication administration;
    a display operable to display, to the participant, one or more of the one or more sets of user prompts for encouraging proper performance of the one or more predetermined movement sequences;
    a video data capture device operable to capture, as captured video information, at least video information of the participant performing one or more of the one or more predetermined movement sequences following the one or more of the one or more sets of user prompts;
    a second storage device for storing the captured video information;

a first processor operable to
output, to the display, a first type of alert that notifies the participant it is time to administer medication,
receive a participant medication administration initiation response following the output of the first type of alert,
output to the display, responsive to receiving the participant medication administration initiation response, the one or more of the one or more sets of user prompts,
receive the captured video information from the second storage device,
automatically analyze the captured video information to confirm whether the participant has properly performed the one or more of the one or more predetermined movement sequences; and
responsive to confirming that the participant has not properly performed the one or more of the one or more predetermined movement sequences, output, to the display, interactive feedback to the participant and an additional one or more of the one or more sets of user prompts to further encourage proper performance of the one or more of the one or more predetermined movement sequences.

9. The system of claim 8, wherein the predefined participant clinical trial protocol is provided by a clinical trial manager.

10. The system of claim 8, comprising a medical database stored on the first or second storage device, wherein the predefined participant clinical trial protocol are stored in the medical database.

11. The system of claim 8, further comprising:
a second processor at a storage and analysis location that is remote from the video data capture device;
a transmission system operable to transmit at least a portion of the captured video information to the storage and analysis location; and
a receipt system operable to receive medication adherence report information from the storage and analysis location, wherein
the second processor is adapted to perform a statistical analysis of the captured video information.

12. The system of claim 8, wherein the first processor is further adapted to:
retrieve medical history information of the participant;
determine whether a to-be-administered medication in the clinical trial is safe for the participant; and
output a warning, when the first processor determines that the to-be-administered medication is not safe for the participant or that the to-be-administered medication is not recognized.

13. The system of claim 12, wherein the first processor is operable to output additional instructions to a medication administrator when the first processor determines that the to-be-administered medication is not safe for the participant.

14. The system of claim 12, wherein the warning comprises additional instructions to a patient receiving the medication according to the predefined participant clinical trial protocol.

15. The system of claim 8, wherein the medication adherence monitoring system is operable to provide live contact with a clinical trial manager through audio and/or video communication.

16. A system for confirming administration of medication, the system comprising:
an authentication apparatus for authenticating a medication manager;
a database comprising prescription administration information for the medication; and
a medication adherence monitoring apparatus, the medication adherence monitoring apparatus comprising
a first storage device operable to store one or more sets of user prompts for encouraging proper performance of one or more predetermined movement sequences indicative of proper medication administration;
a display operable to display to a patient, one or more of the one or more sets of user prompts for encouraging proper performance of the one or more predetermined movement sequences;
a video data capture device operable to capture, as captured video data, at least video data of the patient performing one or more of the one or more predetermined movement sequences in response to the one or more of the one or more sets of user prompts;
a second storage device for storing the captured video data; and
a first processor operable to
output, to the display, a first type of alert that notifies the patient it is time to administer medication,
receive a patient medication administration initiation response following the output of the first type of alert,
output to the display, responsive to receiving the patient medication administration initiation response, the one or more of the one or more sets of user prompts,
receive the captured video data from the second storage device,
automatically compare, as a comparison, the captured video data to additional video data comprising video of the one or more of the one or more predetermined movement sequences,
determine, from the comparison, whether the patient has properly performed the one or more of the one or more predetermined movement sequences,
responsive to determining, from the comparison, that the patient has not properly performed the one or more of the one or more predetermined movement sequences, output, to the display, interactive feedback to the patient and an additional one or more of the one or more sets of user prompts to further encourage proper performance of the one or more of the one or more predetermined movement sequences.

17. The system of claim 16, wherein the additional one or more sets of user prompts comprise real time interactive feedback to aid the patient in properly administering the medication during a current medication administration.

* * * * *